United States Patent
Brandsborg et al.

(12) 
(10) Patent No.: US 6,414,023 B1
(45) Date of Patent: Jul. 2, 2002

(54) DISINFECTING COMPOSITION

(75) Inventors: Erik Brandsborg, Frederiksberg; Preben Borelli, Vanlose, both of (DK)

(73) Assignee: Bifodan A/S, Hundested (DK)

( * ) Notice: Subject to any disclaimer, the term of this patent is extended or adjusted under 35 U.S.C. 154(b) by 0 days.

(21) Appl. No.: 09/646,523

(22) PCT Filed: Mar. 16, 1999

(86) PCT No.: PCT/DK99/00130

§ 371 (c)(1), (2), (4) Date: Oct. 13, 2000

(87) PCT Pub. No.: WO99/46987

PCT Pub. Date: Sep. 23, 1999

(30) Foreign Application Priority Data

Mar. 19, 1998 (GB) ............................................ 0387/98

(51) Int. Cl.[7] ..................... A61K 31/22; A61K 31/225; A61K 31/045

(52) U.S. Cl. ................... 514/546; 514/547; 514/557; 514/724

(58) Field of Search ................................. 514/546, 547, 514/557, 724

(56) References Cited

U.S. PATENT DOCUMENTS

| | | | |
|---|---|---|---|
| 4,067,997 A | 1/1978 | Kabara | 424/312 |
| 4,485,029 A | 11/1984 | Kato et al. | 252/106 |
| 4,921,694 A | 5/1990 | Hoppe et al. | 424/65 |
| 5,569,461 A | * 10/1996 | Andrews | 424/405 |

FOREIGN PATENT DOCUMENTS

| | | |
|---|---|---|
| DE | 4411664 | 10/1995 |
| WO | 9320812 | 10/1993 |
| WO | 9606153 | 2/1996 |
| WO | 9809520 | 3/1998 |
| WO | 9830214 | 7/1998 |

* cited by examiner

*Primary Examiner*—Kevin E. Weddington
(74) *Attorney, Agent, or Firm*—Dykema Gossett PLLC

(57) ABSTRACT

A disinfecting composition includes about 0.01 to 2% by weight 2,4-dichlorobenzyl alcohol, about 0.1 to 10% by weight of glycerylmonolaurate, and about 95 to 99.5 % by weight vehicle such as a mixture of water and alcohol.

9 Claims, No Drawings

DISINFECTING COMPOSITION

BACKGROUND OF THE INVENTION

1. Field of the Invention

This invention relates to a disinfecting composition for human and animal skin, particularly for disinfecting cow udders and teats.

2. The Prior Art

Mastitis, which is a complex and multifactorial disease, is the reaction of milk-producing tissue to influences most often caused by micro-organisms. In response to such microbial influences, a cow's immune system will bring a large number of white blood cells, leucocytes, to the infected area. The result is a battle with the leucocytes trying to engulf and digest the mastitis-causing micro-organisms and the micro-organisms struggling to multiply and get rid of the leucocytes.

As the infection develops, a high number of leucocytes and cells from the tissue, the epithelial cells, will be present in the milk. The leucocytes and epithelial cells are referred to as somatic cells and the number of these cells is an indication of the severity of the infection.

The somatic cell count of milk from uninfected udders is in average less than 200,000 cells/ml; milk from cows with minor infections contains an average of about 200,000–500,000 cells/ml and milk from cows with a major infection shows average counts of more than 500,000 cells/ml.

The presence of large numbers of somatic cells in milk have several adverse events such as:

reduced cheese yields due to lower contents of casein and fat longer coagulation time in cheese production lower stability of milk powder prepared from the milk reduced shelf life of dairy products prepared from such milk and risk of organoleptic defects in e.g. butter.

It is well-known that a number of micro-organisms may cause mastitis. Examples of such micro-organisms are *Strp. agalactiae, Staph. aureus, Streph. uberis, Streph. dysgalactiae, E. coli, P. aeruginosa* and *klebsiella* species.

To prevent mastitis, a variety of disinfecting compostions suitable for use as udder washes and teat dips has been developed. These disinfectants include iodophors, quaternary ammonium compounds, chlorhexidine, sodium hypochlorite, hydrogen peroxide, organic acids and derivatives thereof, dodecylbenzene sulfonic acid and chlorous acid.

This prior art disinfecting compositions are in various forms such as solutions, gels and skin disinfectant wipes.

WO 96/18300 discloses an adherent disinfecting composition comprising a protic acid, a metal chlorite and a gelling agent.

U.S. Pat. No. 5,569,461 discloses an antimicrobial composition which is useful for application to the teats and udders of dairy animals and which comprises one or more propylene glycol mono fatty acid esters in combination with both acidic chelating agents and edible saturated fatty acids.

2,4-dichlorbenzyl alcohol is a compound known to possess lethal activity against a wide range of bacteria, fungi and yeasts and it is also known that compositions containing said compound can be employed to combat bacterial fungal and yeast infections on the skin and are suitable for the preparation of pharmaceutical compositions for oral administration.

It has been noted that some pathogens develop a certain amount of drug resistance to 2,4-dichlorobenzyl alcohol.

It is also known, cf. U.S. Pat. No. 3,123,528, that the bactericidal and fungicidal effects of oral compositions containing 2,4-dichlorobenzyl alcohol can be enhanced by the inclusion of amyl-m-cresol, which is a well-known bactericide and fungicide.

WO 9809520 A1 discloses an antimicrobial ointment for bovine teats comprising an antimicrobial fatty acid monoester of a polyhydroxy alcohol, e.g. glycerol monolaurate, a chelating agent and a vehicle composition comprising petrolatum.

U.S. Pat. No. 4,485,029 A discloses a composition for cleaning, disinfecting and preserving contact lenses comprising water, glyceryl monolaurate and a second antimicrobial agent comprising one or more esters of p-hydroxybenzoic acid, e.g. methyl or propyl paraben. The composition may further contain chelating agents and surfactants.

WO 9606153 A2 discloses a soap formulation comprising a microbial active substance, e.g. a benzyl alcohol such as 2,4-dichlorobenzyl alcohol, hydrotropic agent, surfactant, salt of a fatty acid, dihydric alcohol, monohydric alcohol(s), and balance water.

WO 9320812 A1 discloses an antimicrobial composition comprising (A) a monoclyceride of lauric or monomyristic acid or mixture thereof, (B) a chemical substance selected from a local anesthetic of the amide type, a carbamide, an antibacterial substance in the form of a steroid antibiotic, an imidazole derivative or a nitroimidazole derivative and a 3-6C dial, and (C) optional conventional physiologically acceptable carrier and/or additives. The combination of components (A)+(B) exhibits synergism.

U.S. Pat. No. 4,067,997 A discloses a synergistic microbiocidal composition comprising at least one non-ionic surface-active mono-ester of a 12C aliphatic acid and a polyol, preferably the monolaurin of glycerol, and at least one microbiocide, preferably a phenolic compound. The composition may be applied to the teats of a mammal, such as a cow.

DE 4411664 A1 discloses a synergistic deodorising or antibacterial composition, especially for use in cosmetic or topical preparations, comprising a 3,7,11-trimethyl-2,6,10-dodecatrien-1-ol, a phenylhydroxyalkyl ether having 1-3C in the alkyl part, a glycerol monoester of a short or medium chain length fatty acid, and optionally glycerol monolaurate.

U.S. Pat. No. 4,921,694 A discloses a deodorizing and antimicrobial composition for use in cosmetic or topical formulations containing one or more 3,7,11-trimethyl-2,6,10-dodecatrien-1-ols, a phenylhydroxyalkyl ether having not more than 3C in the alkyl radical and glycerol monolaurate.

When treating a cow's udders and/or teats with a disinfecting composition, there is the risk that part of the disinfecting composition will be introduced into the milk from the cow.

Therefore, it is important that the disinfecting composition contains such components only which are accepted by the health authorities as being non-toxic.

Accordingly, it is an object of the present invention to provide a non-toxic composition which is effective in disinfecting human or animal skin.

It is a further object of the invention to provide a disinfecting composition capable of forming a protective layer or film on the udders and/or teats during intermilking periods so as to prevent reinfection.

A still further object of the invention is to provide a composition which apart from being disinfecting has an anti-inflammatory effect.

These objects and other objects which will appear from the following description are obtained with the disinfecting composition according to the invention which composition comprises:

a) 2,4-dichlorbenzyl alcohol,
b) glycerylmonolaurate and
(c) a vehicle.

Surprisingly, it has been found that the composition of the invention, apart from possessing excellent disinfecting properties, exhibits an anti-inflammatory effect.

Inflammation is the result of extraneously provoked damages of cells or tissue. Such damages may be provoked by chemical and/or physical influences on the skin of humans and animals. Examples of physical influences are strokes, heat, cold, irradiation and electric chock and examples of chemical actions are contacts with acids, bases and allergenes. Inflammation may also be provoked by micro-organisms acting on the skin as opposed to infections which are the result of micro-organisms invading the human or animal body.

In other words, inflammation is a defence mechanism caused by extraneously provoked influences on the skin or tissue. The symptoms may be one of the following: pain, increased skin temperature, swelling, erythema and reduced or ceased function e.g. mastricating efficiency.

The anti-inflammatory effect of the disinfecting compositions of the invention is particularly advantageous when such compositions are to be applied to the udders and teats of milk producing animals such as cows, because the udders and teats are sensitive to influences which may cause inflammation with resulting reduced milk production.

Glycerylmonolaurate which is a well-known disinfectant and is commerically available is a distilled monoglycerate which can be prepared from edible, distilled, fractionated lauric acid. It is known to use glycerylmonolaurate as an emulsifier in food products and as an additive for various types of plastics and/or packaging materials. Furthermore, it is known that it is suitable for surface modifications of fillers and pigments and for starch complexing.

When it is desired to use the disinfecting composition of the invention in the form of a solution, the vehicle is preferably water, an alcohol or a mixture of water and one or more alcohols. Preferred alcohols are ethanol and isopropyl alcohol.

When the composition is to be used in the form of a gel, the vehicle preferably comprises a solvent and a gel-forming hydrocolloid, preferably a gum. A particularly suitable gum is xanthan gum, which is a high molecular weight thixotropic polysaccharide which can be prepared by fermentation of a carbohydrate with *Xanthomononas campestris*. It contains D-glucose and D-mannose as the dominant hexose units along with the D-glucoronic acid and pyruvic acid. Xanthan gum is soluble in water and in a mixture of water and alcohol.

Disfecting compositions in the form of solutions preferably comprises from about 0.01 to 2% by weight of 2,4-dichlorobenzyl alcohol, from about 0.1 to 10% by weight of glycerylmonolaurate and from about 95 to about 99.5% by weight of a vehicle, such as a mixture of water and ethanol. The solution may also contain minor amounts of a thickening agent such as xanthan gum.

Particularly, preferred disinfecting solutions according to the invention comprise from about 0.1 to about 0.3% by weight of 2,4-dichlorobenzyl alcohol, from about 0.5 to about 1.5% by weight of glycerylmonolaurate and from about 98 to about 99.4% of a mixture of water and alcohol.

A particularly preferred disinfecting gel according to the invention comprises from about 0.1 to about 0.3% by weight of 2,4-dichlorobenzyl alcohol, from about 0.5 to about 1,5% by weight of glycerylmonolaurate, from about 0.25 to about 3% by weight of hydrocolloid, the remainder being water, an alcohol or a mixture of water and alcohol.

The disinfecting composition of the invention may be in the form of an ointment and in that case it preferably comprises 0.1–0.3% by weight of 2,4-dichlorobenzyl alcohol, 0.5–1.5% by weight of glycerylmonolaurate, 1–2% by weight of silica, the remainder being vegetable oil.

The invention also relates to a method for the treatment of human or animal skin and in particular the udders and teats of a milk producing animal, said method comprising applying to said skin an effective amount of a composition as described above.

In particular, the invention relates to a method of applying the above described disinfecting composition to the udders and/or the teats of milk producing animals such as cows. When the disinfecting composition is in the form of a solution, it may be applied by washing, dipping, spraying or by using wipes impregnated with said solution.

If the composition is in the form of a gel, it may be applied to the teats so as to form a coating thereon. After drying, the composition forms a protective barrier on the teats.

The invention will be described in further detail with reference to the following non-restrictive examples. Unless otherwise noted, all percentages in the examples are by weight.

EXAMPLE 1

The following components were mixed so as to form a solution for impregnating dairy wipes:

| | |
|---|---|
| 2,4-Dichlorobenzyl alcohol | 0.2% |
| Glycerylmonolaurate (GRINDTEX ML90) | 1.0% |
| Ethanol, 96% | 35.0% |
| Water | 63.8% |
| Total | 100.0% |

EXAMPLE 2

The following components were mixed so as to form a solution suitable as a teat dip:

| | |
|---|---|
| 2,4-Dichlorobenzyl alcohol | 0.2% |
| Glycerylmonolaurate (GRINDTEX ML90) | 1.0% |
| Ethanol, 96% | 35.0% |
| Xanthan gum | 0.5% |
| Water | 63.3% |
| Total | 100.0% |

EXAMPLE 3

The following components were mixed so as to form a cow teat ointment having a sun light screening effect:

| | |
|---|---|
| vegetable oil | 82.3% |
| Titanium dioxide, ultrafine | 15.0% |
| 2,4-Dichlorobenzyl alcohol | 0.2% |
| Silica | 1.5% |
| Glycerylmonolaurate | 1.0% |
| Total | 100.0% |

EXAMPLE 4

This example illustrates the effect of compositions of the invention on several micro-organisms.

The test was carried out according to "Description of a method for a European Suspension Test for the Evaluation of the Efficiency of Disinfectants in Food Hygene" Lab: VD 1985-LK-1130-1, June 1985.

This test comprises adding a suspension of micro-organisms to a solution containing the recommended concentration by weight of the preparation under test.

After a certain period of exposure at a given temperature, the fraction of surviving organisms is determined. Two variants are performed:

(a) with 0.03% bovine albumin in the test solution representing clean conditions, and (b) with 1% bovine albumin in the test solution representing dirty conditions.

The efficacy is assessed on both gram negative and gram positive bacteria and a yeast.

The test strains used were:

*Staphylococcus aureus*

*Streptococcus faecium*

*Pseudomonas aeruginosa*

*Proteus mirabilis*

*Saccharomyces cerevisiae*

The microbicidal effect (ME) determined by said European Suspension Test is calculated on the basis of the formula $$ME = \log N_C - \log N_D$$

wherein $N_c$ = the number of cfu per ml of the test mixture without disinfectant $N_D$ = the number of cfu per ml of the test mixture after the action of the disinfectant.

It is required that a disinfectant preparation in the lowest recommended use dilution induces a microbial effect (ME) of at least 5 logarithmic reduction for each test organism.

As will appear from Tables 1 and 2 which set forth the results obtained by testing the compositions according to Examples 1 and 2, the disinfecting compositions according to both Example 1 and Example 2 passed this test.

The European Suspension Test also comprises a check on the inactivation of the disinfectant, i.e. a check showing that there are no residual, active concentrations of the disinfectant left following inactivation of the disinfectant. In order to pass this test the number of colonies on count plates with disinfectant and inactivation liquid may not be less than half the number of colonies on analogous plates without disinfectant.

As will appear from Tables 1 and 2, both tested compositions pass this test.

TABLE 1

| | Effect of disinfectant | | Check of inactivation | |
|---|---|---|---|---|
| Disinfectant according to Example 1 | 0.03% albumin ME | 1.0% albumin ME | Test mixture without disinfectant | Test mixture with disinfectant and inactivation liquid |
| Staphylococcus aureus | 6.8 | 6.8 | 7.1 | 6.6 |
| Pseudomonas aeruginosa | 6.5 | 6.7 | 7.4 | 6.7 |
| Enterococcus faecium | 6.8 | 7.0 | 6.8 | 6.6 |
| Proteus mirabilis | 6.6 | 6.8 | 6.9 | 6.8 |
| Saccharomyces cerevisiae | 5.1 | 5.1 | 6.0 | 6.0 |

TABLE 2

| | Effect of disinfectant | | Check of inactivation | |
|---|---|---|---|---|
| Disinfectant according to Example 1 | 0.03% albumin ME | 1.0% albumin ME | Test mixture without disinfectant | Test mixture with disinfectant and inactivation liquid |
| Staphylococcus aureus | 6.8 | 6.7 | 7.1 | 6.8 |
| Pseudomonas aeruginosa | 6.6 | 6.6 | 7.4 | 6.6 |
| Enterococcus faecium | 6.8 | 6.7 | 6.8 | 6.8 |
| Proteus mirabilis | 7.0 | 7.1 | 7.3 | 7.0 |
| Saccharomyces cerevisiae | 5.2 | 5.1 | 5.2 | 5.0 |

Comparison Example

The following components were used:

| | |
|---|---|
| "Chemag 2025-S" | 0.6% by weight |
| Glycerol | 5.0% by weight |
| Water | 94.4% by weight | in which "Chemag 2025-S" had the following composition:

| | |
|---|---|
| 2,4-dichlorobenzyl alcohol | 25% by weight |
| Phenoxyethanol[1] | 45% by weight |
| Triethylen glycol[2] | 30% by weight |

[1] Phenoxyethanol is a well-known bactericidal and fungicidal agent.
[2] Triethylen glycol is a compound having anti-microbial properties.

The glycerol and "Chemag 2025-S" were mixed at room temperature and the mixture thus obtained was poured into water during mixing.

The efficacy of the disinfecting composition thus obtained was tested by the above-mentioned European Suspension Test, and the results obtained are set forth in the following Table 3.

TABLE 3

| | Effect of disinfectant | |
|---|---|---|
| | 0.03% albumin ME | 1.0% albumin ME |
| Staphylococcus aureus | 4.1 | <2.0 |
| Pseudomonas aeruginosa | >6.0 | 6.0 |
| Enterococcus faecium | 3.0 | <2.0 |

TABLE 3-continued

|  | Effect of disinfectant | |
| --- | --- | --- |
|  | 0.03% albumin ME | 1.0% albumin ME |
| *Proteus mirabilis* | 5.8 | 5.4 |
| *Saccharomyces cerevisiae* | >5.7 | 1.7 |

It appears from Table 3 that the tested composition does not have a satisfactory effect on *Staphylococcus aureus* and *Enterococcus faecium*, and that it has essentially no effect on *Saccharomyces cerevisiae* under dirty conditions.

A comparison of the test results set forth in Table 3 with those set forth in Tables 1 and 2 indicates that a combination of 2.4-dichlorobenzyl alcohol and glycerylmonolaurate produces a synergistic effect.

What is claimed is:

1. A disinfecting composition comprising
   (a) 2,4-dichlorobenzyl alcohol,
   (b) glycerylmonolaurate and
   (c) a vehicle.
2. A composition according to claim 1, wherein the vehicle is water, an alcohol or a mixture of water and alcohol.
3. A composition according to claim 2, wherein the alcohol is ethanol or isopropyl alcohol.
4. A composition according to any of the preceding claims, wherein the vehicle comprises a hydrocolloid.
5. A composition according to claim 4, wherein the hydrocolloid is xanthan gum.
6. A composition according to claim 1 comprising:
   about 0.01–2% by weight of 2,4-dichlorobenzyl alcohol
   about 0.1–10% by weight of glycerylmonolaurate and
   about 95–99.5% of a vehicle.
7. A composition according to claim 1, comprising:
   about 0.1% to about 0.3% by weight of 2,4-dichlorobenzyl alcohol
   about 0.5 to about 1.5% by weight of glycerylmonolaurate and
   about 98 to about 99.4% by weight of a mixture of water and alcohol.
8. A composition according to claim 1 comprising:
   about 0.1 to about 0.3% by weight of 2,4-dichlorobenzyl alcohol
   about 0.5 to about 1.5% by weight of glycerylmonolaurate
   about 0.25 to about 3% by weight of hydrocolloid,
   the remainder being water, an alcohol or mixture of water and alcohol.
9. A composition according to claim 1 comprising:
   0.1 to 0.3% by weight of 2,4-dichlorobenzyl alcohol
   0.5 to 1.5% by weight of glyceryl monolaurate
   1 to 2% by weight of silica,
   the remainder being vegetable oil.

* * * * *